United States Patent
Kantsevitcha et al.

(10) Patent No.: US 6,863,696 B2
(45) Date of Patent: Mar. 8, 2005

(54) VASCULAR PROSTHESIS

(76) Inventors: Viktoria Kantsevitcha, Lokomotives Iela 72-30, LV-1057 Riga (LV); Eriks Masteiko, Lacu Iela 10b, LV-2010 Jurmala (LV); Leonids Ribickis, Dzirnavu Iela 74/76-51, LV-1011 Riga (LV)

( * ) Notice: Subject to any disclaimer, the term of this patent is extended or adjusted under 35 U.S.C. 154(b) by 0 days.

(21) Appl. No.: 10/803,154

(22) Filed: Mar. 17, 2004

(65) Prior Publication Data

US 2004/0221623 A1 Nov. 11, 2004

Related U.S. Application Data

(63) Continuation-in-part of application No. 10/775,826, filed on Feb. 10, 2004, which is a continuation-in-part of application No. 10/204,009, filed on Oct. 10, 2002, now Pat. No. 6,709,467.

(30) Foreign Application Priority Data

Feb. 16, 2000 (LV) .............................................. P-00-21

(51) Int. Cl.⁷ .................................................. A61F 2/06
(52) U.S. Cl. .................................. 623/901; 139/387 R
(58) Field of Search ........................ 139/387 R, 383 R, 139/384 R; 623/1.1, 1.41, 1.44, 1.45, 1.46, 1.47, 1.48, 901

(56) References Cited

U.S. PATENT DOCUMENTS

| | | | |
|---|---|---|---|
| 4,784,659 A | 11/1988 | Fleckenstein |
| 4,816,028 A | 3/1989 | Kapadia |
| 4,892,539 A | 1/1990 | Koch |
| 5,127,919 A | 7/1992 | Ibrahim |
| 5,800,514 A | 9/1998 | Nunez |
| 5,904,714 A | 5/1999 | Nunez |

FOREIGN PATENT DOCUMENTS

| | | |
|---|---|---|
| EP | 0 122 744 A1 | 10/1984 |
| EP | 0 183 365 A2 | 6/1986 |
| EP | 0 464 755 A1 | 1/1992 |
| GB | 2 153 685 A | 8/1985 |
| LV | 12175 B | 12/1998 |
| WO | WO 92/03107 | 3/1992 |

*Primary Examiner*—Danny Worrell
(74) *Attorney, Agent, or Firm*—Colin P. Abrahams

(57) ABSTRACT

A tubular vascular prosthesis with a uniform velour outer layer has an elementary unit of tubing composed of a double velour outer layer, made from polyester yarn, the middle layer, made from two polyester yarns, positioned between two strained polyurethane monofilament yarns and four polyurethane yarn monofilaments, the smooth inner surface and linking of all three layers made of polyester wefts, the between filaments filled with aqueous gelatin-glycerol solution.

4 Claims, 4 Drawing Sheets

Shows the cross-section of the elementary unit of the prosthesis wall.

Shows the cross-section of the elementary unit of the prosthesis wall.

Shows the prosthesis deformation index λ as function of the internal blood pressure [mm Hg].

Shows the elongation of the polyurethane monofilament as function of straining force P [cN].

Shows the thickness of yarn A [mm] as a function of strain.

VASCULAR PROSTHESIS

CROSS REFERENCE TO RELATED APPLICATIONS

This application is a continuation-in-part application of U.S. patent application Ser. No. 10/775,826 filed Feb. 10, 2004, which is a continuation-in-part application of U.S. patent application Ser. No. 10/204,009 filed Oct. 10, 2002, now U.S. Pat. No. 6,709,467.

FIELD OF THE INVENTION

The present invention relates to a vascular prosthesis useful in reconstructive surgery for inborn vessel anomaly, aterosclerotic damage and/or injury.

BACKGROUND OF THE INVENTION

Vessel prostheses from textile material are known, in particular frilled vascular prostheses (Latvian patent No. 10836), composed of low-elasticity porous polyester and elastic polyurethane monofilaments, forming a double-layered woven structure. The drawback of this prosthesis is the increased thickness of its walls and leaking of blood due to imperfection of wall structure.

Another known prosthesis, endowed with higher elasticity (Latvian patent No. 12175), is knit from complex polyester and polyurethane monofilaments, and formed with a velour surface. The drawback of this prosthesis is its porosity, allowing increased leakage of blood, and unraveling ends of the prosthesis, encumbering its joining with a natural vessel.

SUMMARY OF THE INVENTION

In one aspect, the present invention therefore provides a vascular prosthesis of various dimensions, which has good mechanical characteristics, substantially or reduced non-raveling ends, a structure with low permeability for blood and good acceptance for ingrowth of living tissue for natural sealing of prosthesis walls.

DESCRIPTION OF THE INVENTION

In one embodiment, the invention relates to producing a tubular vascular prosthesis of complex triple-layered structure, wherein the structure of the outer layer of the prosthesis is similar to that of the natural arterial vessel, which is consequently impregnated by aqueous glycerol and gelatin solution to seal the pores between the yarns.

Figure 1:
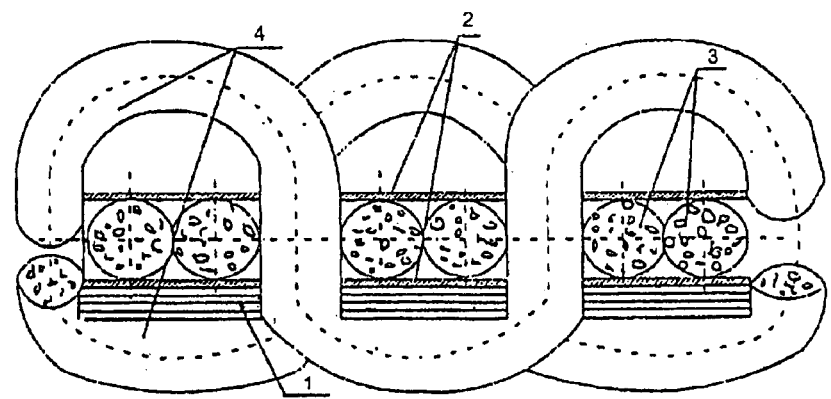
FIG. 1 is a cross section of an elementary unit of the prosthesis wall in accordance with one embodiment of the invention.

The required structure, in accordance with one embodiment of the invention, is formed from biologically inert multifilament polyester and monofilament polyurethane warps and wefts, the elastic prosthesis in tubular form being woven in a complex pattern, where each elementary unit of the weave (FIG. 1) is composed of a double velour outer layer, made from polyester yarn (4), a middle layer from two polyester yarns (3), positioned between two strained and/or stretched polyurethane monofilament yarns (2) and four polyurethane monofilament yarns (1), the smooth inner surface made of polyester wefts (4). All three layers are woven together by said polyester yarns. The product thus formed is then impregnated in a vacuum by and/or with an aqueous solution of gelatin and glycerol, containing, in one preferred embodiment, 12% gelatin and 12–15% glycerol. The polyurethane warps (1) and wefts (2) are strained in the weaving process up to 200%.

The weaving method and specific polyurethane properties preferably provides for a complex woven structure, where the warps and wefts can be strained up to 200% and relaxed after the weaving process, forming a tight tubular prosthesis with a velour outer surface, permitting it to be ingrown by living tissue, the prosthesis being deformable to adapt to different loads, and preferably maintaining the necessary strength. The ability to pulsate with the rhythm of blood flow is essential for living processes after the replacement therapy. The polyurethane monofilament tends to imitate or emulate the elastane, while the polyester filaments tend to imitate or emulate the collagen fibers of a natural blood vessel, thus providing both for elasticity and strength.

Figure 2:
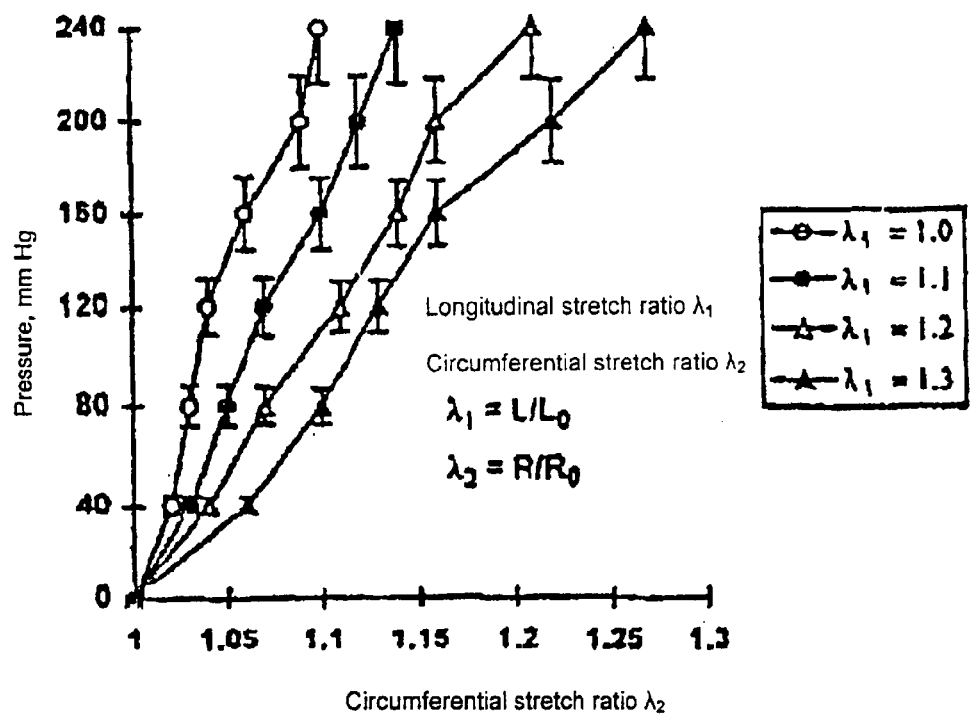
FIG. 2 is a graph showing the prosthesis deformation index λ as a function of the internal blood pressure [mmHg]
Figure 3:
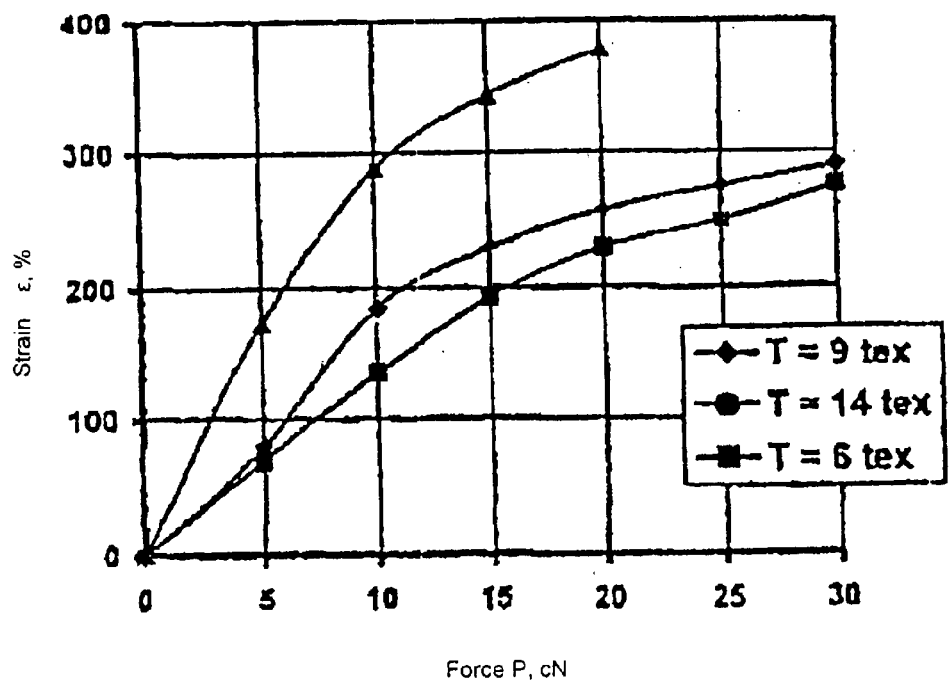
FIG. 3 is a graph showing the elongation of the polyurethane monofilament as a function of straining force P[cN]
Figure 4:
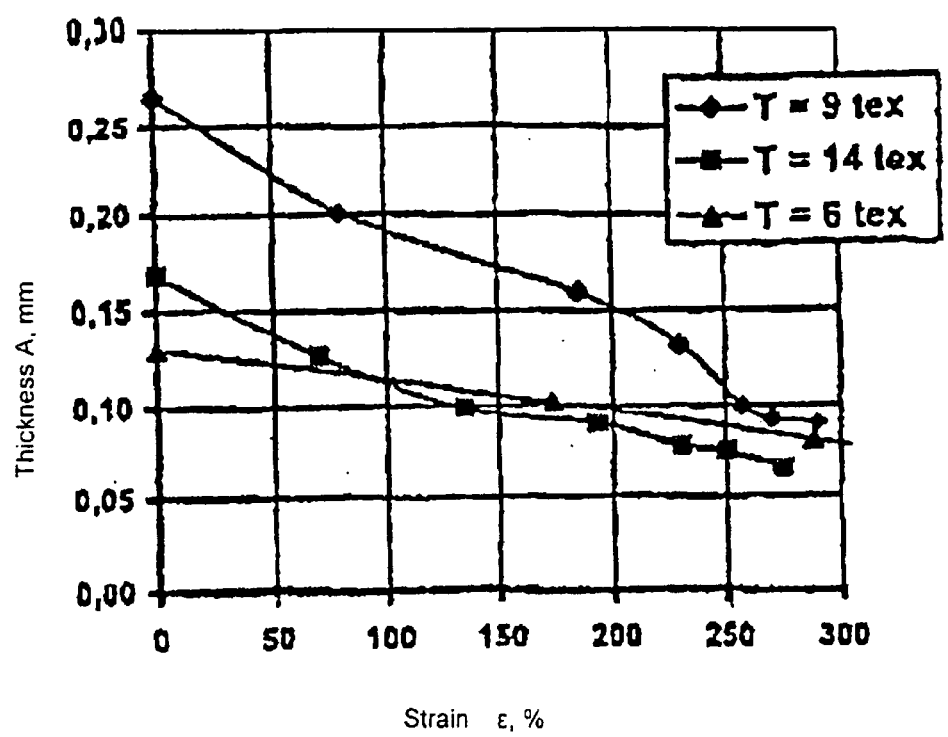
FIG. 4 is a graph showing the thickness of yarn A [mm] as a function of strain

By changing the relative proportion of polyurethane filaments to polyester filaments in the elementary unit of prosthesis, it is possible to control the elasticity of the prosthesis. The preferred structure in accordance with the invention is deformable in a peripheral direction up to about 50% and longitudinally up to about 10–12% at the internal blood pressure of about 240 mm Hg, preserving the necessary flow properties (see FIG. 2).

The method in accordance with one embodiment of the invention for impregnating the prosthesis in a vacuum by the aqueous solution comprising about 12% (w/v) gelatin and from about 12 to about 15% (w/v) glycerol provides for formation of elastic membranes between the filaments and filling of pores. The smooth surface of the inner wall of prosthesis obtained after impregnation, in accordance with one aspect of the invention, helps to reduce and prevent the leakage of blood through the wall of the prosthesis and may conveniently avoid or reduce the necessity to impregnate the prosthesis by the patient's blood before the implantation of the prosthesis. It also preferably provides for quick formation of endothelium and intima.

The weaving method of one aspect of the invention provides for manufacturing of pulsing arterial prostheses of different size; by changing the number of polyurethane monofilament warp yarns on a warp beam, the diameter of the prosthesis ca be varied, while by variation of the linear density of polyurethane yarns the thickness of the prosthesis walls can be changed. Moreover, the method of the invention preferably produces a prosthesis with substantially non-raveling ends, or ends where unraveling is reduced, resulting in a more convenient implantation without the necessity to additionally treat the ends against unraveling.

EXAMPLE

Materials and Methods

In one embodiment of the invention, an automatic loom was used for weaving. The number of warp yarns per cm was 35. The yarns used in a woven product are typically strained prior to weaving. The present technology requires a specific straining of warps on the beam.

The polyurethane monofilaments were strained in the loom by a force of 25 cN/yarn for yarns of linear density of T=9–14 Tex or 10 cN/yarn for yarns of linear density T=6 Tex. The relative strain constitutes approximately 250–290% (see FIG. 2), and the thickness of yarn after straining is reduced to approximately 50–64% of the starting thickness. After passing the breast beam, the yarns relax, the strain being reduced to approximately 100–125%.

EXAMPLE

For producing a 6 mm diameter prosthesis, two warp beams were prepared with multifilament polyester yarns with linear density of 9.1 Tex, the number of yarns being 33. Another two warp beams were prepared with polyurethane monofilament with linear density 7–7.1 Tex, the number of yarns being 33. The polyurethane monofilaments were strained in the weaving zone to approximately 200%. In each shed one polyester yarn and two polyurethane yarns are carried by rapier on the first run. On the reverse run the rapier again carries one polyester and two polyurethane yarns, thus four polyurethane yarns and two polyester yarns are introduced. On the consecutive runs the shed is changed in accordance with the weaving pattern.

The elementary unit was produced in four picking repeats. The number of runs depended on the necessary length of prosthesis.

After weaving the prosthesis was impregnated by aqueous glycerol and gelatin solution comprising about 12% (w/v) gelatin and about 12% (w/v) glycerol in a vacuum at approximately 90° C. temperature. The impregnated prosthesis was dried to form gelatine-glycerol membranes in the pores of prosthesis.

The invention is not limited to details described and variations with in the scope of the claims may be made.

What is claimed is:

1. A method for preparing a woven vascular prosthesis with a uniform velour outer layer characterized in that the tubing is woven in a complex weave, wherein the elementary unit of said tubing is composed of double velour outer layer, made from polyester yarn, the middle layer, made from two polyester yarns, positioned between two strained polyurethane monofilament yarns and four polyurethane yarn monofilaments, the smooth inner surface and linking of all three layers made of polyester wefts, with subsequent impregnating of said tubing under vacuum by aqueous gelatin-glycerol solution.

2. The method of claim 1, wherein the polyurethane monofilaments are strained up to 200%.

3. The method of claim 1, wherein the said solution contains gelatin about 12% (w/v) and glycerol from about 12 to about 15% (w/v).

4. A tubular vascular prosthesis with a uniform velour outer layer, characterized in that the elementary unit of said tubing is composed of a double velour outer layer, made from polyester yarn, the middle layer, made from two polyester yarns, positioned between two strained polyurethane monofilament yarns and four polyurethane yarn monofilaments, the smooth inner surface and linking of all three layers made of polyester wefts, the between filaments filled with aqueous gelatin-glycerol solution.

* * * * *